US012788694B2

(12) United States Patent
Pielak

(10) Patent No.: US 12,788,694 B2
(45) Date of Patent: Nov. 10, 2026

(54) CHEMICAL COMPOSITIONS PROVIDING LONG-LASTING SKIN pH CONTROL FOR IMPROVING SKIN-BARRIER FUNCTION AND TREATMENT OF SKIN-BARRIER DISORDERS

(71) Applicant: Soteri Skin, Inc., El Cerrito, CA (US)

(72) Inventor: Rafal M. Pielak, El Cerrito, CA (US)

(73) Assignee: Soteri Skin, Inc., El Cerrito, CA (US)

( * ) Notice: Subject to any disclaimer, the term of this patent is extended or adjusted under 35 U.S.C. 154(b) by 397 days.

(21) Appl. No.: 18/253,173

(22) PCT Filed: Apr. 25, 2022

(86) PCT No.: PCT/US2022/071895
§ 371 (c)(1),
(2) Date: May 16, 2023

(87) PCT Pub. No.: WO2022/232764
PCT Pub. Date: Nov. 3, 2022

(65) Prior Publication Data

US 2024/0000681 A1 Jan. 4, 2024

Related U.S. Application Data

(60) Provisional application No. 63/299,239, filed on Jan. 13, 2022, provisional application No. 63/179,998, filed on Apr. 26, 2021.

(51) Int. Cl.

| | |
|---|---|
| ***A61K 36/00*** | (2006.01) |
| ***A61K 8/365*** | (2006.01) |
| ***A61K 8/67*** | (2006.01) |
| ***A61K 8/68*** | (2006.01) |
| ***A61K 8/73*** | (2006.01) |
| ***A61Q 19/00*** | (2006.01) |

(52) U.S. Cl.
CPC .............. *A61K 8/365* (2013.01); *A61K 8/675* (2013.01); *A61K 8/68* (2013.01); *A61K 8/735* (2013.01); *A61Q 19/00* (2013.01)

(58) Field of Classification Search
None
See application file for complete search history.

(56) References Cited

U.S. PATENT DOCUMENTS

| | | | |
|---|---|---|---|
| 4,263,313 | A | 4/1981 | Eckert et al. |
| 8,758,805 | B2 | 6/2014 | Rabouille |
| 9,101,662 | B2 | 8/2015 | Tamarkin et al. |
| 9,895,393 | B2 | 2/2018 | Trumbore et al. |
| 10,973,749 | B2 | 4/2021 | Sverdlove et al. |
| 2019/0015358 | A1 | 1/2019 | Stasko et al. |
| 2020/0188517 | A1 | 6/2020 | Shanler et al. |
| 2020/0306165 | A1 | 10/2020 | Sverdlove et al. |

FOREIGN PATENT DOCUMENTS

| | | | |
|---|---|---|---|
| WO | 2022232764 | A1 | 11/2022 |

OTHER PUBLICATIONS

Lukic et al. (2021) Cosmetics 8:69 (18 pages). (Year: 2021).*
Cavalcanti et al. (2021) Current Pharmaceutical Design 27: 2289-2298. (Year: 2021).*
Das et al. (2020) Scientific Reports 10: 12288. (Year: 2020).*
Lambers et al. (2006) Intern. J. Cosmetic Science 28: 359-370. (Year: 2006).*
Lin et al. (2005) J. Invest. Dermatol. 125: 826-832. (Year: 2005).*
Adam, R. (2008). "Skin Care of the Diaper Area," Pediatr Dermatol. 25(4):427-433.
Ali, S. M. et al (Jan. 10, 2013). "Skin pH: From Basic SciencE to Basic Skin Care," Acta Dermato-Venereologica 93(3):261-267.
Banandemon et al. (May 12, 2020). "Atomy Absolute Cellactive Serum. Anti-Aging Serum," retrieved from the Internet https://incidecoder.com/products/atomy-absolute-cellactive-serum, 38 pages.
Bedi, G. et al. (Nov. 2022). "Open Label, Single Arm, Interventional Multi-Centered Study to Evaluate the Efficacy and Biophysical Response of Topical Soteri Skin Cream in Following Skin Conditions: Atopic Dermatitis, Eczema, Psoriasis and Rosacea," International Journal of Research in Dermatology 8(6):543-550.
Blaak, J. et al. (Sep. 2011). "Treatment of Aged Skin with a pH 4 Skin Care Product Normalizes Increased Skin Surface pH and Improves Barrier Function: Results of a Pilot Study," Journal of Cosmetics, Dermatological Sciences and Applications 1(3):50-58.
Boothe, W. D. (2017). "Atopic Dermatitis: Pathophysiology," Adv Exp Med Biol. 1027:21-37.
Bouwstra, J. A. et al. (Dec. 2006, e-pub. Jul. 11, 2006). "The Skin Barrier in Healthy and Diseased State," Biochim. Biophys. Acta—Biomembr. 1758(12):2080-2095.
Choi, H. K. et al. (Dec. 2017, e-pub. Sep. 21, 2017). "Phytosphingosine enhances moisture level in Human Skin Barrier Through Stimulation of the Filaggrin Biosynthesis and Degradation Leading to NMF Formation," Arch Dermatol Res. 309(10):795-803.
Danby, S. G. et al. (2018). "pH in Atopic Dermatitis," Curr Probl Dermatol. 54:95-107.
Dharmage, S. C. et al. (Jan. 2014). "Atopic Dermatitis and the Atopic March Revisited," Allergy 69(1):17-27.
Du Plessis, J. L. et al. (2018). "Measurement of Skin Surface pH," Curr Probl Dermatol 54:19-25.
Eberlein-Konig, B. et al. (May 2000). "Skin Surface pH, Stratum Corneum Hydration, Trans-Epidermal Water Loss and Skin Roughness Related to Atopic Eczema and Skin Dryness in a Population of Primary School Children," Acta Derm Venereol 80(3):188-191.
Elias, P. M. (Jul. 2008). "Skin Barrier Function," Curr Allergy Asthma Rep. 8(4):299-305, 6 pages.
Elias, P. M. (Mar. 2015, e-pub. Feb. 17, 2015). "Stratum Corneum Acidification: How and Why?" Exp Dermatol. 24(3):179-180.

(Continued)

*Primary Examiner* — Russell G Fiebig
(74) *Attorney, Agent, or Firm* — Bajwa IP Law Firm; Haris Zaheer Bajwa

(57) ABSTRACT

Provided are compositions that are formulated for use on human skin, and designed to maintain optimal skin surface pH over an extended period of time. Provided herein are also methods of using such compositions for treating skin barrier function and associated disorders.

21 Claims, 8 Drawing Sheets

(56) References Cited

OTHER PUBLICATIONS

Elias, P. M. et al. (Nov. 2017). "The How, Why and Clinical Importance of Stratum Corneum Acidification," Exp Dermatol. 26(11):999-1003.
Epstein, W. L. et al. (Oct. 1965). "Cell Renewal in Human Epidermis," Arch Dermatol. 92(4):462-468.
Hachem, J. P. et al. (Feb. 2010). "Acute Acidification of Stratum Corneum Membrane Domains Using Polyhydroxyl Acids Improves Lipid Processing and Inhibits Degradation of Corneodesmosomes," J Invest Dermatol. 130(2):500-510.
Hatano, Y. et al. (Jul. 2009). "Maintenance of an Acidic Stratum Corneum Prevents Emergence of Murine Atopic Dermatitis," J Invest Dermatol 129(7):1824-1835.
Imokawa, G. et al. (Apr. 1999). "Decreased Level of Ceramides in Stratum Corneum of Atopic Dermatitis: An Etiologic Factor in Atopic Dry Skin?" J Invest Dermatol. 96(4):523-526.
Inoue, H. et al. (Oct. 2010, e-pub. Jul. 21, 2010). "Citric Acid Inhibits a Bacterial Ceramidase and Alleviates Atopic Dermatitis in an Animal Model," J Antibiot (Tokyo) 63(10):611-613.
International Search Report and Written Opinion of the International Search Authority mailed on Jul. 1, 2022, for PCT Application No. PCT/US2022/071895, filed on Apr. 25, 2022, 11 pages.
Kilic, A. et al. (Jun. 2019). "Skin Acidification with a Water-in-Oil Emulsion (pH 4) Restores Disrupted Epidermal Barrier and Improves Structure of Lipid Lamellae in the Elderly," J Dermatol. 46(6):457-465.
Kim, J. et al. (Mar. 2019). "Pathophysiology of Atopic Dermatitis: Clinical Implications," Allergy Asthma Proc 40 (2):84-92.
Lambers, H. et al. (Nov. 2006). "Natural Skin Surface pH is on Average Below 5, Which is Beneficial for its Resident Flora," Int J Cosmet Sci. 28(5):359-370.
Lee, H. J. et al. (Oct. 2014). "Topical Acidic Cream Prevents the Development of Atopic Dermatitis- and Asthma-like Lesions in Murine Model," Exp Dermatol. 23(10):736-741.
Lee, N. R. et al. (Dec. 2016). "Application of Topical Acids Improves Atopic Dermatitis in Murine Model by Enhancement of Skin Barrier Functions Regardless of the Origin of Acids," Ann Dermatol 28(6):690-696.
Levin, J. et al. (May 2008). "Human Skin Buffering Capacity: An Overview," Skin Res Technol. 14(2):121-126.
Lowe, A. J. et al. (Feb. 1, 2018). "The Skin as a Target for Prevention of the Atopic March," Ann Allergy Asthma Immunol 120(2):145-151.
Madison, K. C. et al. (Aug. 2003). "Barrier Function of the Skin: 'La Raison d'etre' of the Epidermis," Journal of Investigative Dermatology 121(2):231-241.
Mao-Qiang, M. et al. (Aug. 1993). "Fatty Acids are Required for Epidermal Permeability Barrier Function," J Clin Invest. 92(2):791-798.
Mauro, T. et al. (Apr. 1998). "Barrier Recovery is Impeded at Neutral pH, Independent if Ionic Effects: Implications for Extracellular Lipid Processing," Arch Dermatol Res. 290(4):215-222.
Mohrenschlager, M. et al. (Mar. 2006). "The Course of Eczema in Children Aged 5-7 Years and its Relation to Atopy: Differences Between Boys and Girls," Br J Dermatol. 154(3):505-513.
Ohman, H. et al. (Oct. 1998). "The pH Gradient Over the Stratum Corneum Differs in X-Linked Recessive and Autosomal Dominant Ichthyosis: A Clue to the Molecular Origin of the Acid Skin Mantle?" J Invest Dermatol. 111 (4):674-677.
Pielak, R. et al. (Aug. 11, 2022). "Skin Surface pH and Its Implication in Skin Health," Chapter 36 in Handbook of Cosmetic Science and Technology, Dreher, F. ed., CRC Press: Boca Raton, FL, 6 pages.
Proksch, E. et al. (Mar.-Apr. 2003). "Skin Lipids and Epidermal Differentiation in Atopic Dermatitis," Clin Dermatol. 21(2):134-144.
Rawlings, A. V. et al. (Jun. 1996). "Effect of Lactic Acid Isomers on Keratinocyte Ceramide Synthesis, Stratum Corneum Lipid Levels and Stratum Corneum Barrier Function," Arch Dermatol Res. 288(7):383-390.
Schreml, S. et al. (Nov. 2014). "Skin pH in the Elderly and Appropriate Skin Care," EMJ Dermatol. 2:86-94.
Seidenari, S. et al. (Jun. 1998). "Baseline Biophysical Parameters in Subjects with Sensitive Skin," Contact Dermatitis 38(6):311-315.
Seidenari, S. et al. (Nov. 1995). "Objective Assessment of the Skin of Children Affected by Atopic Dermatitis: A Study of pH, Capacitance and TEWL in Eczematous and Clinically Uninvolved Skin," Acta Derm Venereol. 75 (6):429-433.
Smith, A. R. et al. (Jan. 2017). "The Skin as a Route of Allergen Exposure: Part I. Immune Components and Mechanisms," Curr Allergy Asthma Rep. 17(1):6, 18 pages.
Soteri Skin. (Oct. 25, 2021). "Ingredients," WayBackMachine Archive, located at: https:/soteriskin.com/pages/ingredients, 3 pages.
Soteri Skin. (Oct. 25, 2021). "Skin Barrier Function 101," WayBackMachine Archive, located at: https://soteriskin.com/blogs/skincare-articles/understanding-the-skin-barrier-function-and-why-it-matters, 6 pages.
Soteri Skin. (Oct. 25, 2021). "Skin pH and Skin Health," WayBackMachine Archive, located at: https://soteriskin.com/blogs/skincare-articles/why-maintaining-an-acidic-ph-should-be-the-most-important-part-of-your-skincare-routine, 7 pages.
Soteri Skin. (Oct. 25, 2021). "The Science," WayBackMachine Archive, located at: https://soteriskin.com/pages/our-products-and-the-science-behind-them, 7 pages.
Sparavigna, A. et al. (Oct. 2006). "Cutaneous pH in Children Affected by Atopic Dermatitis and in Healthy Children: A Multicenter Study," Skin Research and Technology 5(4):221-227.
Surber, C. et al. (2018). "The Acid Mantle: A Myth or an Essential Part of Skin Health?" Curr Probl Dermatology 54:1-10.
Takagi, Y. et al. (May 1999). "Beta-glucocerebrosidase Activity in Mammalian Stratum Corneum," Mammalian Stratum Corneum 40(5):861-869.
Trombino, S. et al. (Jan. 2009, e-pub. May 29, 2008). "Synthesis And Antioxidant Activity Evaluation of a Novel Cellulose Hydrogel Containing Trans-Ferulic Acid," Carbohydrate Polymers 75(1):184-188.
Wohlrab, J. et al. (2018). "pH and Buffer Capacity of Topical Formulations," Curr Probl Dermatology 54:123-131.
Wohlrab, J. et al. (Jun. 27, 2014). "Niacinamide—Mechanisms of Action and its Topical Use in Dermatology," Skin Pharmacol Physiol. 27(6):311-315.
Zlotogorski, A. (Aug. 1987). "Distribution of Skin Surface pH on the Forehead and Cheek of Adults," Archives of Dermatological Research 279:398-401.
Soteri Skin. (Oct. 25, 2021). "Research and Testing," WayBackMachine Archive, located at: http://web.archive.org/web/20211025071009/https:/soteriskin.com/pages/research-and-testing, 6 pages.

* cited by examiner

Before

After

Before

After

CHEMICAL COMPOSITIONS PROVIDING LONG-LASTING SKIN pH CONTROL FOR IMPROVING SKIN-BARRIER FUNCTION AND TREATMENT OF SKIN-BARRIER DISORDERS

CROSS-REFERENCE TO RELATED APPLICATIONS

This application is a national stage application under 35 U.S.C. § 371 of International Application No. PCT/US2022/071895, filed internationally on Apr. 25, 2022, which claims priority to U.S. Provisional Patent Application No. 63/299,239, filed Jan. 13, 2022, and U.S. Patent Application Ser. No. 63/179,998, filed Apr. 26, 2021, which are incorporated herein by reference in their entireties.

FIELD

The present disclosure relates generally to skin topical compositions and formulations, and more specifically to a topical formulation designed to maintain optimal skin surface pH over an extended period of time.

BACKGROUND

The formation of lipophilic components of Stratum Corneum (SC) involves several pH-dependent enzymes. Two key lipid-processing enzymes, beta-glucocerebrosidase and acidic sphingomyelinase, have pH optima of 5.6 and 4.5, respectively. Both lipid-processing enzymes are involved in the synthesis of ceramides, which are critical components of the permeability barrier.

Optimal skin surface pH does not only influence the barrier homeostasis, but also affects SC integrity, cohesion, and desquamation. An elevated pH increases the activity of serine proteases, kallikrein 5 and 7, which are involved in the desquamation and degradation of corneodesmosomes.

Acidic pH is also essential for normal skin flora growth, whereas pathogenic bacteria, such as *Staphylococcus aureus*, thrives at a neutral pH level. A number of factors, including both endogenous and exogenous elements, affect skin pH.

Various studies have shown that elevations of pH in normal skin create a disturbed barrier, linked to increased activity of serine proteases and reduced activities of ceramide-generating enzymes. Therefore, changes in skin pH greatly affect skin function and skin health, as well as contribute to a number of skin conditions, such as atopic dermatitis, eczema, rosacea, psoriasis, and acne.

BRIEF SUMMARY

In some aspects, provided is a solution to irregularities and skin conditions which are related to and/or caused by instability and fluctuations in the skin pH level. The formulations provided herein are designed such that the skin pH level is maintained at an optimal level in order to allow for key enzymatic reactions involved in skin barrier synthesis and maintenance.

In some aspects, provided are topical formulations with optimized pH and pH buffer capacity to provide long-lasting optimal skin surface pH and prevent pH fluctuations. In some embodiments, the topical formulations are pH optimized for key enzymatic reactions and processes such as ceramide production. Specifically, in some variations, the topical formulations support the function of beta-glucocerebrosidase and acid sphingomyelinase. In some embodiments, the topical formulations are pH optimized for supporting the skin microbiome. In some variations, the topical compositions provided herein are formulated as creams, lotions, serums, cleanser, toners, foundations, and/or similar.

In certain aspects, provided is a topical composition with an optimal pH buffer capacity at around pH 4.7. In some variations, the optimal pH buffer capacity is at pH 4.7 +/−0.3. In one embodiment, the topical composition comprises:

a) an acid comprising a plurality of carboxylic acid groups, wherein at least one carboxylic acid group has a pKa around 4.7, at least one carboxylic acid group has a pKa between 4.7 and 6.5, and at least one carboxylic acid group has a pKa between 3 and 4.7; and its conjugate base; or b) an acid having one carboxylic acid group, wherein the acid has a pKa of around 4.7, and wherein the acid has a molecular weight of at least 140 g/mol; and its conjugate base; or c) a plurality of acids comprising one or more carboxylic acid groups, wherein at least one acid has a pKa around 4.7, at least one acid has a pKa between 4.7 and 6.5, and at least one acid has a pKa between 3 and 4.7, and wherein each acid has a molecular weight of at least 140 g/mol; and the conjugate base of at least one of the acids; or d) an acid having at least one chemical group that remains ionized at pH around 4.7; and optionally at least one supporting compound capable of accepting at least some hydrogen ions within a pH range between 3 and 5.5, wherein the topical composition, when applied to human skin, maintains a skin surface pH of around 4.7 for at least 6 hours.

In some variations of the foregoing, the acid(s) present in the topical composition may fall within one or more categories (a)-(d) above.

In certain aspects, provided is a system, comprising a container containing any of the topical compositions described herein.

In other aspects, provided is a method comprising: applying any of the topical compositions described herein to skin of a human, wherein the skin has a skin surface pH, and wherein the skin surface pH is maintained at around 4.7 for at least 6 hours.

In some embodiments, the topical formulations are pH optimized to match the skin surface pH for treatment of skin barrier function and associated disorders. Examples of such disorders or skin conditions include acne, psoriasis, rosacea, xerosis, and various forms of eczema including, for example, atopic dermatitis and contact dermatitis. In some embodiments, the topical formulations are pH optimized to treat different skin conditions resulting from dysregulated skin surface pH. In other embodiments, the topical formulations have optimized pH and pH buffer capacity to support wound healing (for example, chronic wounds such as in diabetes).

All of the listed skin conditions are either consequences of the disrupted skin barrier or result in skin barrier disruption. Consequently, improving the skin barrier can provide some level of treatment. By maintaining skin surface pH, the topical formulations provided herein improve skin barrier function and consequently can provide improvements in these conditions.

The following document aims to provide an accurate and detailed description of the present invention without limiting the scope of the invention, and the accompanying figures are only intended to help illustrate the present invention. Thus, the accompanying figures do not limit the scope of the invention in any way, shape or form.

DESCRIPTION OF THE FIGURES

The present application can be understood by reference to the following description taken in conjunction with the accompanying figures.

DETAILED DESCRIPTION

Figure 1A:
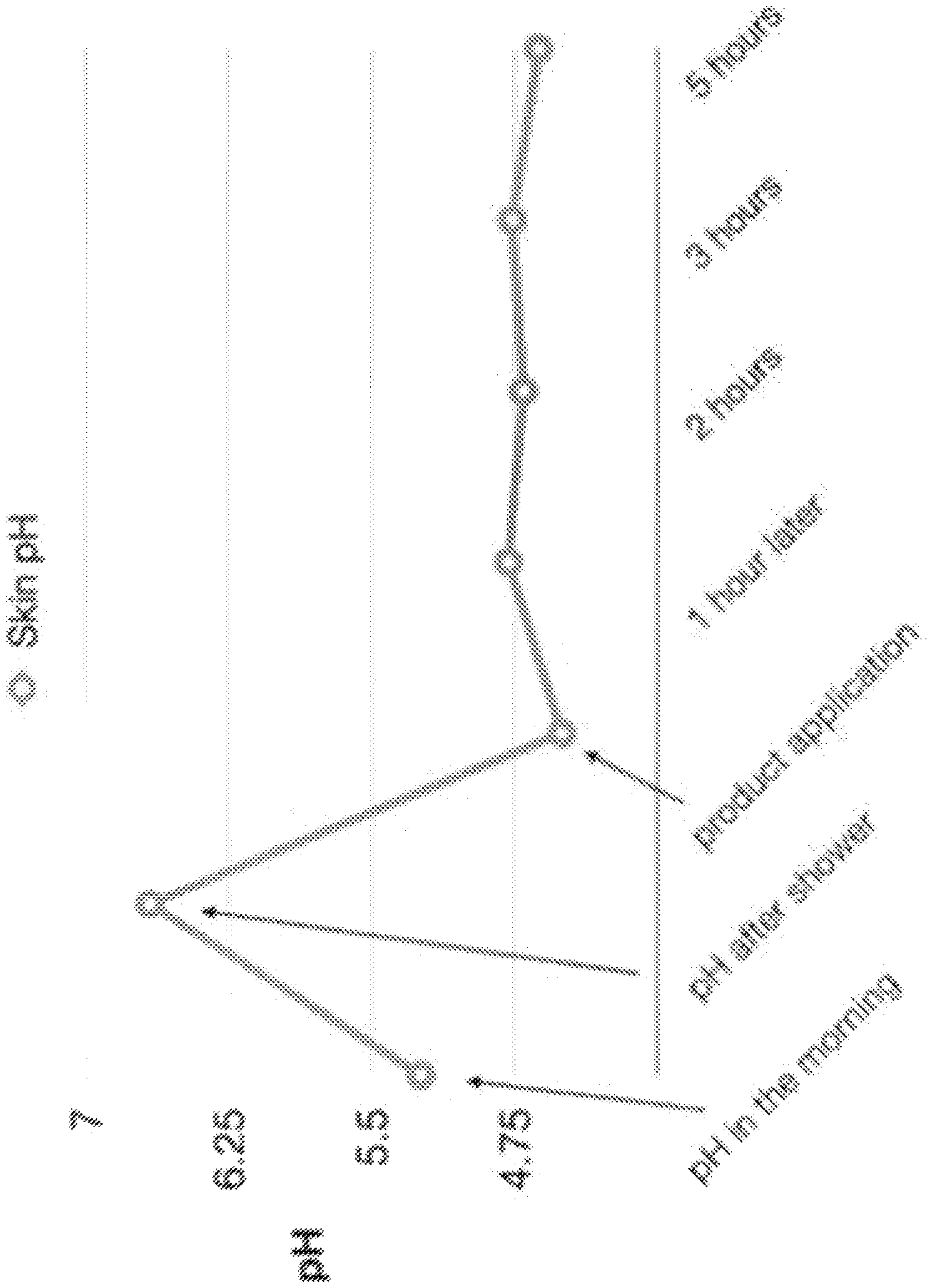
FIG. 1A is a graph of the stabilization of the pH skin level after topical application of an exemplary formulation provided herein.

All illustrations, drawings, visual aid and/or figures accompanying the following document are for the purpose of describing the present invention and are not intended to limit the scope of the present invention.

In some aspects, provided is a topical formulation that can maintain optimal skin surface pH levels over an extended period of time. In some embodiments, the topical formulation maintains the skin surface pH level at around 4.7.

The topical formulation maintains the skin surface pH level at an optimal level for key enzymatic reactions involved in the skin barrier synthesis and maintenance as seen in FIG. 1. Maintaining the skin surface pH at the optimal pH level (e.g., pH around 4.7) may be better tolerated, safer, and have superior outcomes on skin health and treatment of skin disorders than temporary, acute acidification with solutions adjusted to a pH well below the natural skin pH. The compositions provided herein are formulated to maintain steady pH of the skin at the optimal level over at least 6 hours, at least 8 hours, or at least 12 hours, and prevent pH fluctuations.

In some embodiments, the topical formulations provided herein include a pH buffering system with strong buffer capacity around pH 4.7, the optimal pH or natural pH of healthy skin. In some variations, the pH buffering system includes hydrogen ion acceptors and donors that have pKa values that span from pKa 3 to 5.5, optimally with at least one molecule with a pKa around 4.7. In some variations, the pH buffering system includes hydrogen ion acceptors and donors that do not readily diffuse through the skin, which would affect their concentration on the skin surface and consequently result in a pH shift over time. In some variations, the pH buffering system is not irritating and is well tolerated even for sensitive skin or skin affected by eczema or psoriasis.

In some variations, "around 4.7" in the context of pH or pKa refers to 4.7 +/−0.3.

In certain embodiments, provided herein are therapeutic effects of the topical formulations, particularly for the treatment of dermatoses, such as eczema, as seen in FIG. 2.

Traditional topical products containing water and oils (emulsions) typically contain preservatives that prevent microbial growth. Preservatives can be irritating for skin prone to dermatitis (eczema). In fact, preservatives are one of the most common sensitizers and irritants in contact dermatitis and atopic eczema. The topical formulations provided herein are self-preserving by combination of low pH, high ionic strength, and low water availability. This provides additional benefits in the treatment of skin affected by eczema or other forms of dermatitis.

The components and uses of the topical formulations provided herein are described in further detail below.

Components of the Topical Formulation

The compositions provided herein are formulated for topical use on human skin. In one aspect, provided is a topical composition with an optimal pH buffer capacity at around pH 4.7. In some embodiments, the topical composition, when applied to human skin, maintains a skin surface pH of 4.7 +/−0.3 for at least 6 hours, at least 8 hours, or at least 12 hours; or between 6 hours and 24 hours.

In certain embodiments, the composition provided herein comprises a strong pH buffering capacity at a pH level ranging between 3 to 6.5, which provides long lasting control over skin surface pH and prevents skin surface pH fluctuations.

In some variations, the composition comprises an acid comprising a plurality of carboxylic acid groups, wherein at least one carboxylic acid group has a pKa around 4.7, at least one carboxylic acid group has a pKa between 4.7 and 6.5, and at least one carboxylic acid group has a pKa between 3.0 and 4.7. In some variations, the composition further comprises the conjugate base of the acid. In yet some variations of the foregoing, the acid remains charged at around pH 4.7. In certain variations, the acid is citric acid. In one embodiment, the composition comprises citric acid and citrate. In one variation, the citrate is sodium citrate. In another embodiment, the composition comprises citric acid, sodium citrate, and gluconic acid. In yet another embodiment, the composition further comprises gluconate.

In other variations, the composition comprises an acid having one carboxylic acid group and its conjugate base, wherein the acid has a pKa of 4.7 +/−0.3, and wherein the acid has a molecular weight of at least 140 g/mol. In certain variations, the acid has a molecular weight between 140 g/mol and 450 g/mol. In one variation, the acid is ferulic acid.

In yet other variations, the composition comprises a plurality of acids comprising one or more carboxylic acid groups, wherein at least one acid has a pKa around 4.7, at least one acid has a pKa between 4.7 and 6.5, and at least one acid has a pKa between 3.0 and 4.7, and wherein each acid has a molecular weight of at least 140 g/mol. In some variations, the plurality of acids comprises at least ferulic acid, gluconic acid, or citric acid, or any combination thereof.

In certain variations of the foregoing, the composition comprises a polymer comprising multiple carboxylic acid groups having the pKa in any of the ranges stated above; and/or having a molecular size that prevents its permeation. In some variations, such molecular size is a molecular weight of at least 140 g/mol, or between 140 g/mol and 450 g/mol. In one variation, the composition may comprise a large hydrophilic polymer, such as a carbohydrate that has a pKa in any of the ranges stated above. In such variation, the carbohydrate does not necessarily need to be ionized at pH 4.7 to limit its permeation, as the size will be sufficient to limit its permeation. On the other hand, in another variation, a smaller hydrophilic molecule, such as citric acid benefits from the ionization at pH 4.7 to limit its permeation.

In yet other variations, the composition comprises an acid having at least one chemical group that remains ionized at pH around 4.7. In one variation, the composition comprises an acid having at least one chemical group that remains ionized at pH around 4.7; and its conjugate base.

In certain embodiments, the composition comprises one or more buffers composed of a high concentration mixture of acids and bases. In certain variations, the acids and bases for the present invention comprise at least one pKa around 4.7 or multiple pKa values between 3 and 6.5.

In some variations, the composition comprises a mixture of acids and bases that are both water and lipid-soluble. The water and lipid-soluble characteristics help the mixture of acids and bases to maintain an optimal pH value on the skin surface due to the mixture of water containing a compartment surrounded by lipid sheets on the skin surface.

In certain variations of the foregoing, the composition may further include at least one supporting compound capable of accepting at least some hydrogen ions within a pH range between 3 and 5.5. In certain variations, the supporting compound is capable of accepting at least some hydrogen ions within a pH range between 4 and 5. In some variations, the supporting compound decreases skin irritation. In some variations, the composition is capable of maintaining a skin surface pH of 4.7 +/−0.3 in the absence of a supporting compound. In some variations, the supporting compound contributes to the capability of the composition to maintain a skin surface pH of 4.7 +/−0.3.

In certain variations, a supporting compound is a medium chain fatty acid having a pKa between 4.5 and 5.5. In certain variations of the foregoing, the medium chain fatty acid is caprylic acid, capric acid, or lauric acid, or any combination thereof. In certain variations, a supporting compound is a carbohydrate having a pKa between 3.0 and 4.0. In certain variations of the foregoing, the carbohydrate is hyaluronic acid. In certain variations, a supporting compound is an amino acid having a pKa between 3 and 5. In certain variations of the foregoing, the amino acid is glutamic acid. In one variation, the composition comprises citric acid, gluconic acid, and glutamic acid.

In one embodiment, the composition comprises 3-10% weight for weight (w/w) citric buffer (citric acid/sodium citrate, pKa 3.13, pKa 4.76 and pKa 6.4), 2-6% w/w medium-chain triglycerides (pKa 5.3-4.8), and 0-2% w/w ferulic acid (pKa ~4.6). In another embodiment, the composition comprises 5-30% weight for weight (w/w) citric buffer (citric acid/sodium citrate, pKa 3.13, pKa 4.76 and pKa 6.4), 2-6% w/w medium-chain triglycerides (pKa 5.3-4.8), and 0-2% w/w ferulic acid (pKa ~4.6).

In some embodiments, the composition further comprises carboxylic acids such as lactic acid, glycolic acid, malic acid, tartaric acid, mandelic acid, tropic acid, salicylic acid, lactobionic acid, glucuronic acid, gluconic acid, ferulic acid, hyaluronic acid, amino acids, or fatty acids, or any combination thereof.

In certain embodiments, the composition may further comprise at least one skin barrier renewal component, at least one anti-inflammatory component, at least one anti-microbial component, at least one humectant, at least one emollient and/or emulsifier, or any combination thereof. In certain variations, at least one skin barrier renewal component comprises a ceramide complex, niacinamide, or phytosphingosine, or any combination thereof. In certain variations of the foregoing, the ceramide complex comprises ceramides, cholesterol, and at least one free fatty acid or a precursor thereof. In certain variations of the foregoing, the ceramides are Ceramide NP, Ceramide AP, or Ceramide EOP, or any combination thereof. In certain variations of the foregoing, the precursor of at least one free fatty acid is sodium lauroyl lactylate. In certain variations of the foregoing, at least one anti-inflammatory and/or anti-microbial component comprises sunflower seed oil, coconut oil, shea butter, or colloidal oatmeal, or any combination thereof. In certain variations of the foregoing, at least one humectant comprises hyaluronic acid, amino acids, glycerin, or xantham gum, or any combination thereof. In certain variations of the foregoing, at one emollient and/or emulsifier comprises caprylic triglyceride, cetearyl alcohol, or ceteareth-20, or any combination thereof.

For example, in certain embodiments, the composition may also contain other ingredients commonly found in cosmetic products such as water, glycerin, ceramides, cholesterol, triglycerides, oils, hyaluronic acid, and/or similar.

In one aspect, provided is a composition comprising: citric acid and sodium citrate, and optionally gluconic acid; a ceramide complex; niacinamide; phytosphingosine; and hyaluronic acid.

In another aspect, provided is a composition comprising: citric acid and sodium citrate, and optionally gluconic acid; a ceramide complex; niacinamide; phytosphingosine; hyaluronic acid; sunflower seed oil; coconut oil; shea butter; and colloidal oatmeal.

In certain embodiments, the acid is present in an amount between 1% and 30% by weight of the total topical composition.

Additionally, the combination of the low pH level and high buffering capacity and ionic strength of the composition provided herein prevents microbial growth. In some embodiments, the composition has no detectable amounts of steroids, added fragrance, sulfates, formaldehyde, alcohol, or added preservatives, or any combination thereof. In one embodiment, the composition is vegan.

Additionally, in some variations, the topical compositions provided include, for example, creams, lotions, serums, cleansers, toners, foundations and/or similar.

Uses of the Topical Formulations

In some embodiments, the compositions provided herein maintain an optimal environment for the key enzymatic reactions involved in skin barrier homeostasis, for instance reactions involving beta-glucocerebrosidase and acid sphingomyelinase. In some variations, the optimal pH and strong pH buffering capacity from the composition are capable of supporting a healthy skin microbiome. As previously mentioned, the low pH level and high ionic strength reduce microbial growth and therefore comprise a self-preserving property.

In some embodiments, the chemical composition provided comprises an optimal pH and strong pH buffering capacity for the treatment of skin barrier function and associated disorders.

In one aspect, provided is a method comprising applying a topical composition to the skin of a human, wherein the skin has a skin surface pH, and wherein the skin surface pH is maintained at around 4.7 for at least 6 hours. In some variations, the skin surface pH is maintained at 4.7 +/−0.3 for at least 6 hours. In some variations, the skin surface pH is maintained at 4.7 +/−0.3 for at least 8 hours. In some variations, the skin surface pH is maintained at 4.7 +/−0.3 for at least 12 hours.

In one aspect, provided is a method comprising applying a topical composition to the skin of a human, for treating skin barrier function and associated disorders. In some variations, the human has a skin disorder. In certain variations of the foregoing, the human has a skin condition resulting from dysregulated skin surface pH.

In certain variations, the human has atopic dermatitis, acne, eczema, psoriasis, rosacea, or xerosis, or any combination thereof. In some variations, applying the topical composition to the skin of the human supports wound healing. In certain variations of the foregoing, applying the topical composition to the skin of the human supports the healing of chronic wounds from diabetes.

In some variations, the human has eczema. In certain variations, applying the topical composition to the skin of the human treats eczema flares, or reduces itch, or a combination thereof. In some variations, applying the topical composition to the skin of the human reduces eczema flare frequency and severity.

In certain embodiments, the chemical composition of the topical application provided is capable of treating skin disorders such as but not limited to different forms of eczema treatment (for example, atopic dermatitis treatment or contact dermatitis treatment), acne treatment, psoriasis treatment, rosacea treatment, xerosis treatment, or similar.

Furthermore, in certain embodiments, the chemical composition of the topical application provided is also capable of treating any skin disorder which results from dysregulated skin surface pH.

It is to be understood that many other possible modifications and variations can be made without departing from the spirit and scope of the invention. Obvious changes, modifications and substitutions may be made by those skilled in the art to achieve the same purpose of the invention.

The exemplary embodiments are merely examples and are not intended to limit the scope of the invention. It is intended that the present invention cover all other embodiments that are within the scope of the appended claims and their equivalents.

ENUMERATED EMBODIMENTS

The following enumerated embodiments are representative of some aspects of the invention.

1. A topical composition with an optimal pH buffer capacity at around pH 4.7, comprising:
   a) an acid comprising a plurality of carboxylic acid groups, wherein at least one carboxylic acid group has a pKa around 4.7, at least one carboxylic acid group has a pKa between 4.7 and 6.5, and at least one carboxylic acid group has a pKa between 3 and 4.7; and its conjugate base; or
   b) an acid having one carboxylic acid group, wherein the acid has a pKa of around 4.7, and wherein the acid has a molecular weight of at least 140 g/mol; and its conjugate base; or
   c) a plurality of acids comprising one or more carboxylic acid groups, wherein at least one acid has a pKa around 4.7, at least one acid has a pKa between 4.7 and 6.5, and at least one acid has a pKa between 3 and 4.7, and wherein each acid has a molecular weight of at least 140 g/mol; and the conjugate base of at least one of the acids; or
   d) an acid having at least one chemical group that remains ionized at pH around 4.7; and its conjugate base; and optionally at least one supporting compound capable of accepting at least some hydrogen ions within a pH range between 3 and 5.5, wherein the topical composition, when applied to human skin, maintains a skin surface pH of around 4.7 for at least 6 hours.

2. The topical composition of embodiment 1, comprising an acid comprising a plurality of carboxylic acid groups, wherein at least one carboxylic acid group has a pKa about 4.7, at least one carboxylic acid group has a pKa between 4.7 and 6.5, and at least one carboxylic acid group has a pKa between 3 and 4.7; and its conjugate base, and optionally wherein the acid remains charged at around pH 4.7.
3. The topical composition of embodiment 2, wherein the acid is citric acid.
4. The topical composition of embodiment 3, comprising: citric acid and sodium citrate; or citric acid, sodium citrate, and gluconic acid.
5. The topical composition of embodiment 1, comprising an acid having one carboxylic acid group and its conjugate base, wherein the acid has a pKa around 4.7, and wherein the acid has a molecular weight of at least 140 g/mol, or between 140 g/mol and 450 g/mol.
6. The topical composition of embodiment 5, wherein the acid is ferulic acid.
7. The topical composition of embodiment 1, comprising a plurality of acids comprising one or more carboxylic acid groups, wherein at least one acid has a pKa around 4.7, at least one acid has a pKa between 4.7 and 6.5, and at least one acid has a pKa between 3 and 4.7, and wherein each acid has a molecular weight of at least 140 g/mol.
8. The topical composition of embodiment 7, wherein the plurality of acids comprises at least one of ferulic acid, gluconic acid, and citric acid, or a combination thereof.
9. The topical composition of embodiment 1, comprising an acid having at least one chemical group that remains ionized at pH around 4.7.
10. The topical composition of any one of embodiments 1 to 9, wherein at least one supporting compound comprises at least one medium chain fatty acid, at least one carbohydrate, at least one amino acid having a pKa between 3 and 5, or any combination thereof.

11. The topical composition of embodiment 10, wherein at least one fatty acid has a pKa between 4.5 and 5.5.
12. The topical composition of embodiment 10, wherein at least one fatty acid is caprylic acid, capric acid, or lauric acid, or any combination thereof.
13. The topical composition of any one of embodiments 10 to 12, wherein at least one carbohydrate has a pKa between 3 and 4.
14. The topical composition of any one of embodiments 10 to 12, wherein at least one carbohydrate is hyaluronic acid.
15. The topical composition of any one of embodiments 10 to 14, wherein at least one amino acid having a pKa between 3 and 5 is glutamic acid.
16. The topical composition of any one of embodiments 1 to 15, further comprising at least one skin barrier renewal component, at least one anti-inflammatory component, at least one anti-microbial component, at least one humectant, at least one emollient and/or emulsifier, or any combination thereof.
17. The topical composition of embodiment 16, wherein at least one skin barrier renewal component comprises a ceramide complex, niacinamide, or phytosphingosine, or any combination thereof.
18. The topical composition of embodiment 17, wherein the ceramide complex comprises ceramides, cholesterol, and at least one free fatty acid or a precursor thereof.
19. The topical composition of embodiment 18, wherein the precursor of at least one free fatty acid is sodium lauroyl lactylate.
20. The topical composition of any one of embodiments 16 to 19, wherein at least one anti-inflammatory and/or anti-microbial component comprises sunflower seed oil, coconut oil, shea butter, or colloidal oatmeal, or any combination thereof.
21. The topical composition of any one of embodiments 16 to 20, wherein at least one humectant comprises hyaluronic acid, amino acids, glycerin, or xantham gum, or any combination thereof.
22. The topical composition of any one of embodiments 16 to 21, wherein at one emollient and/or emulsifier comprises caprylic triglyceride, cetearyl alcohol, or ceteareth-20, or any combination thereof.
23. The topical composition of embodiment 1, comprising:
    citric acid and sodium citrate, and optionally gluconic acid;
    a ceramide complex;
    niacinamide;
    phytosphingosine; and
    hyaluronic acid.
24. The topical composition of embodiment 23, further comprising:
    sunflower seed oil;
    coconut oil;
    shea butter; and
    colloidal oatmeal.
25. The topical composition of any one of embodiments 1 to 24, wherein the optimal pH buffer capacity is at pH 4.7 +/−0.3; and wherein the topical formulation, when applied to human skin, maintains a skin surface pH of 4.7 +/−0.3.
26. The topical composition of any one of embodiments 1 to 25, wherein the topical formulation, when applied to human skin, maintains a skin surface pH of 4.7 +/−0.3 for at least 8 hours or at least 12 hours.
27. The topical composition of any of embodiments 1 to 26, wherein the acid is present in an amount of between 1% and 30% by weight of the total topical composition.
28. The topical composition of any one of the preceding embodiments, wherein the topical composition is formulated as a lotion.
29. The topical composition of any one of the preceding embodiments, wherein the topical composition has no detectable amounts of steroids, added fragrance, sulfates, formaldehyde, alcohol, or added preservatives, or any combination thereof.
30. The topical composition of any one of the preceding embodiments, wherein the composition is vegan.
31. A system, comprising: a container containing a topical composition of any one of embodiments 1 to 30.
32. The system of embodiment 31, wherein the container is an airtight bottle.
33. A method comprising: applying a topical composition of any one of embodiments 1 to [0089]30 to skin of a human, wherein the skin has a skin surface pH, and wherein the skin surface pH is maintained at around 4.7 for at least 6 hours.
34. The method of embodiment 33, wherein the skin surface pH is maintained at 4.7 +/−0.3 for at least 6 hours.
35. The method of embodiment 33, wherein the skin surface pH is maintained at 4.7 +/−0.3 for at least 8 hours or at least 12 hours.
36. The method of any one of embodiments 33 to 35, for treating skin barrier function and associated disorders.
37. The method of any one of embodiments 33 to 35, wherein the human has a skin disorder.
38. The method of any one of embodiments 33 to 35, wherein the human has a skin condition resulting from dysregulated skin surface pH.
39. The method of any one of embodiments 33 to 35, wherein the human has atopic dermatitis, acne, eczema, psoriasis, rosacea, or xerosis, or any combination thereof.
40. The method of any one of embodiments 33 to 35, for supporting wound healing.
41. The method of any one of embodiments 33 to 35, wherein the human has eczema.
42. The method of embodiment 41, wherein applying the topical composition to the skin of the human treats eczema flares, or reduces itch, or a combination thereof.
43. The method of embodiment 42, wherein applying the topical composition to the skin of the human reduces eczema flare frequency and severity.

EXAMPLES

The presently disclosed subject matter will be better understood by reference to the following Examples, which are provided as exemplary of the invention, and not by way of limitation.

Example 1

Skin pH Measurements Using Exemplary Topical Formulation

This example tests an exemplary topical formulation product on human skin by measuring skin pH as follows: 1. Morning skin surface pH; 2. Skin surface pH increase after shower; 3. Skin surface pH recovery after product application-skin pH equilibration at the optimal skin surface pH; and 4. Skin surface pH maintenance over a 5-hour period.

The exemplary topical formulation includes water, citric acid, sodium citrate, glycerin, capric/caprylic triglycerides, cetearly alcohol, ceteareth-20, sodium lauroyl lactylate, hyaluronic acid, ceramide NP, ceramide AP, ceramide EOP, phytoshpingosine, and cholesterol.

The topical formulation was applied to the skin on the forearm of a human test subject. The subject was instructed not to wash the skin after product application. The pH was measured 1) before shower, 2) after shower, 3) immediately after product application, 4) 1 hour after product application, 5) 2 hours after product application, 6) 3 hours after product application, 7) 5 hours after product application.

Results are summarized in FIG. 1A. Based on the results, the use of the topical formulation surprisingly not only corrected elevated pH immediately after product application but also maintained the corrected pH over 5 hours.

Figure 1B:
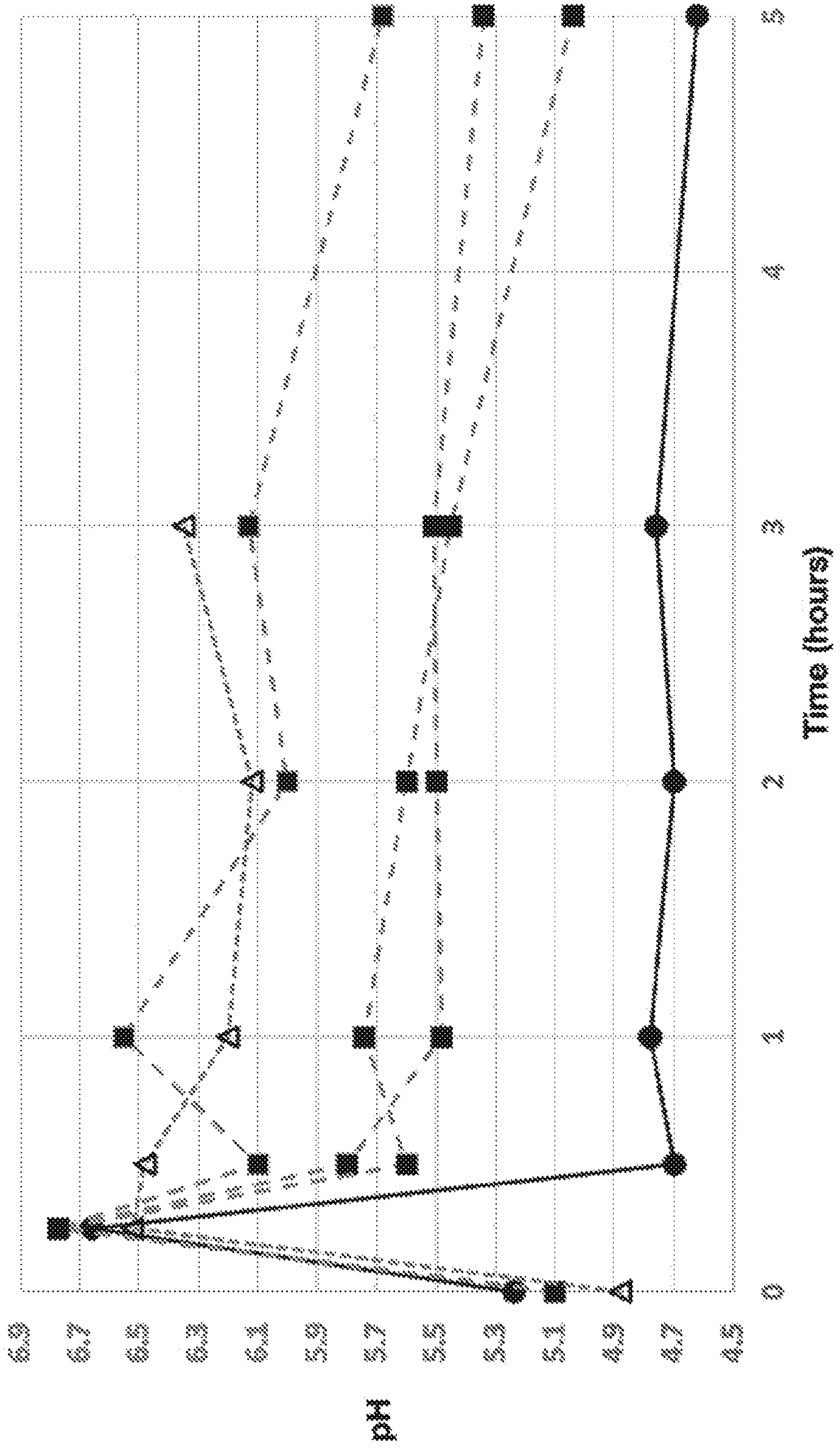
FIG. 1B is a graph comparing an exemplary formulation provided herein (solid line with circle markers) to three different topical creams commercially available on the market (dashed lines with square markers) and no product (dashed line with triangle markers) by measuring skin pH.

FIG. 1B compares an exemplary topical formulation (solid line with circle markers) on human skin to three different topical creams currently available on the market (dashed lines with square markers) and no product (dashed line with triangle markers) by measuring the skin pH as follows: 1. Morning skin surface pH; 2. Skin surface pH increase after shower; 3. Skin surface pH after production application, and 4. Skin surface pH over a 1, 2, 3, and 5 hour period.

The three commercially available topical creams tested had a higher than optimal pH and were unable to maintain the skin surface pH at the optimal level.

Example 2

Eczema Treatment Tests

With reference to FIGS. 2A-2D, 4A, 4B, 5A, 5B, 6A, 6B, 7A and 7B, the formulation was surprisingly observed to not only help to heal eczema flares and reduce itch, but also provide long term reduction in flare frequency and severity.

Figure 2A:
FIG. 2A is a facial area before topical application of an exemplary formulation provided herein.
Figure 2B:
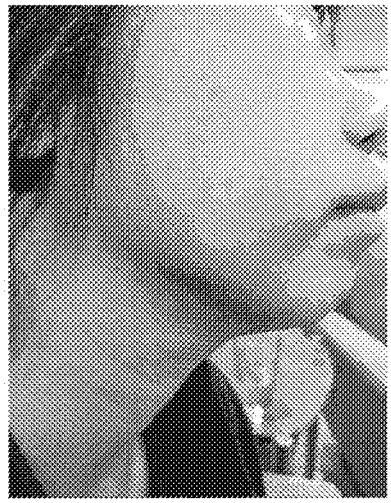
FIG. 2B is a facial area after 11 days of consistent topical application of an exemplary formulation provided herein.
Figure 2C:
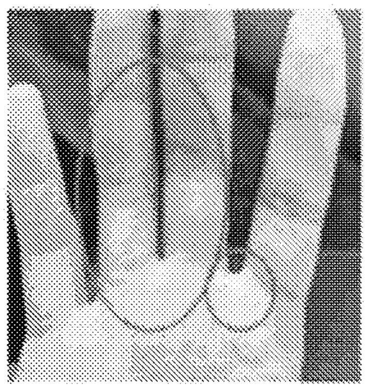
FIG. 2C is a hand before topical application of an exemplary formulation provided herein.
Figure 2D:
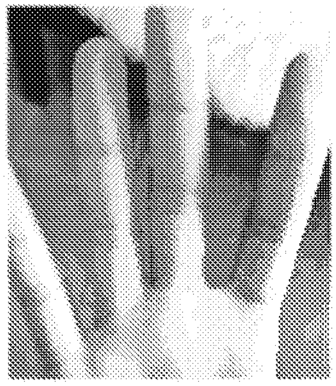
FIG. 2D is a hand after 14 days of consistent topical application of an exemplary formulation provided herein.
Figure 4A:
FIG. 4A is a neck area before topical application of an exemplary formulation provided herein.
Figure 4B:
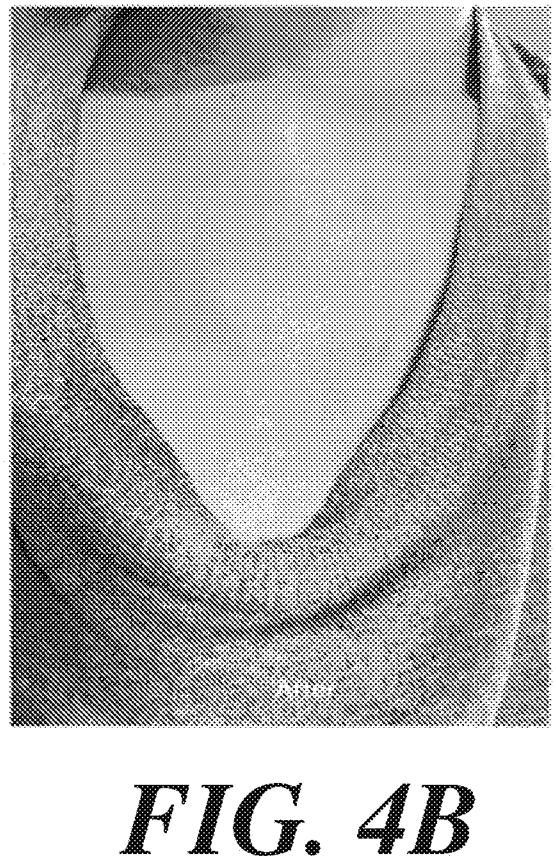
FIG. 4B is a neck area after 7 days of consistent topical application of an exemplary formulation provided herein.
Figure 5A:
FIG. 5A is a shin area before topical application of an exemplary formulation provided herein.
Figure 5B:
FIG. 5B is a shin area after 7 days of consistent topical application of an exemplary formulation provided herein.
Figure 6A:
FIG. 6A is an area of an arm near the elbow before topical application of an exemplary formulation provided herein.
Figure 6B:
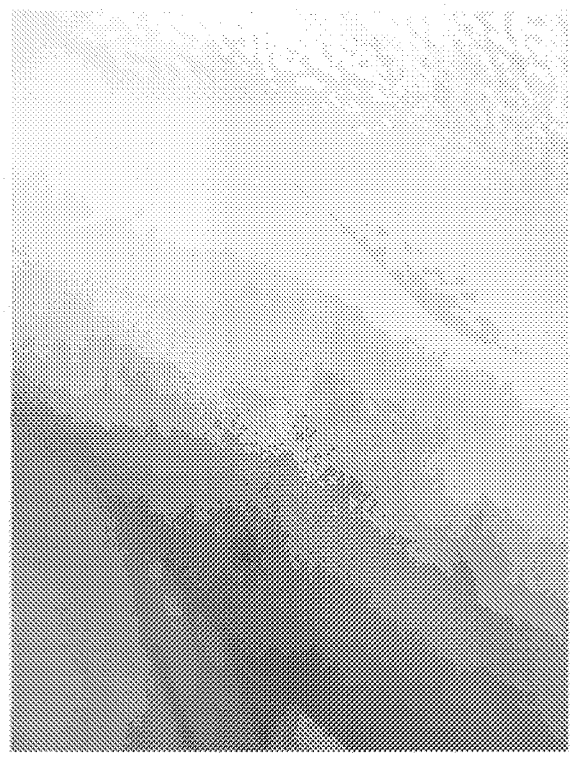
FIG. 6B is an area of an arm near the elbow after 14 days of consistent topical application of an exemplary formulation provided herein.
Figure 7A:
FIG. 7A is an area of an arm near the wrist before topical application of an exemplary formulation provided herein.
Figure 7B:
FIG. 7B is an area of an arm near the wrist after 14 days of consistent topical application of an exemplary formulation provided herein.

FIGS. 2A-2D show flare healing after 11 days when the formulation is applied to the face, see FIGS. 2A (before) and 2B (after), as well as after 14 days when the formulation is applied to the hands, see FIGS. 2C (before) and 2D (after). FIGS. 4A (before) and 4B (after) show flare healing after 7 days when the formulation is applied to the neck area. FIGS. 5A (before) and 5B (after) show flare healing after 7 days when the formulation is applied to the shin area. FIGS. 6A (before) and 6B (after) show flare healing after 14 days when the formulation is applied to the arm near the elbow. FIGS. 7A (before) and 7B (after) show flare healing after 14 days when the formulation is applied to the arm near the wrist.

In some cases, such as for the subject initially photographed in FIG. 2, the formulation was surprisingly found to completely break the eczema cycle, and the subject became eczema free for over 8 months with consistent product application. The formulation also reduced dependence on topical steroids, and some of the subjects became completely free of eczema flares while using the formulations.

The exemplary topical formulation used in FIGS. 2A and 2B comprises water, citric acid, sodium citrate, glycerin, capric/caprylic triglycerides, cetearly alcohol, ceteareth-20, sodium lauroyl lactylate, hyaluronic acid, niacinamide, ceramide NP, ceramide AP, ceramide EOP, phytoshpingosine, cholesterol, and xanthan gum.

The exemplary topical formulation used in FIGS. 4A, 4B, 5A, 5B, 6A, 6B, 7A and 7B comprises water, citric acid, sodium citrate, glycerin, capric/caprylic triglycerides, cetearly alcohol, ceteareth-20, sodium lauroyl lactylate, hyaluronic acid, niacinamide, ceramide NP, ceramide AP, ceramide EOP, phytoshpingosine, cholesterol, and xanthan gum.

Example 3

Skin Surface Correction

This example demonstrates the effect of an exemplary formulation provided herein on skin surface pH after initial pH disruption (due to skin washing with soap and water).

The exemplary topical formulation comprises water, citric acid, sodium citrate, glycerin, capric/caprylic triglycerides, cetearly alcohol, ceteareth-20, sodium lauroyl lactylate, hyaluronic acid, niacinamide, ceramide NP, ceramide AP, ceramide EOP, phytoshpingosine, cholesterol, oat, amino acids, and xanthan gum.

The topical formulation was applied to the skin of 2 human test subjects on one forearm and one cheek, and no product was applied to the second forearm, the second cheek, or the nose. The subject was instructed not to wash the skin after product application. The pH was measured 1) before shower, 2) after shower, 3) immediately after product application, and 4) at about 2, 4, 6, and 12 hours after product application.

Figure 3:
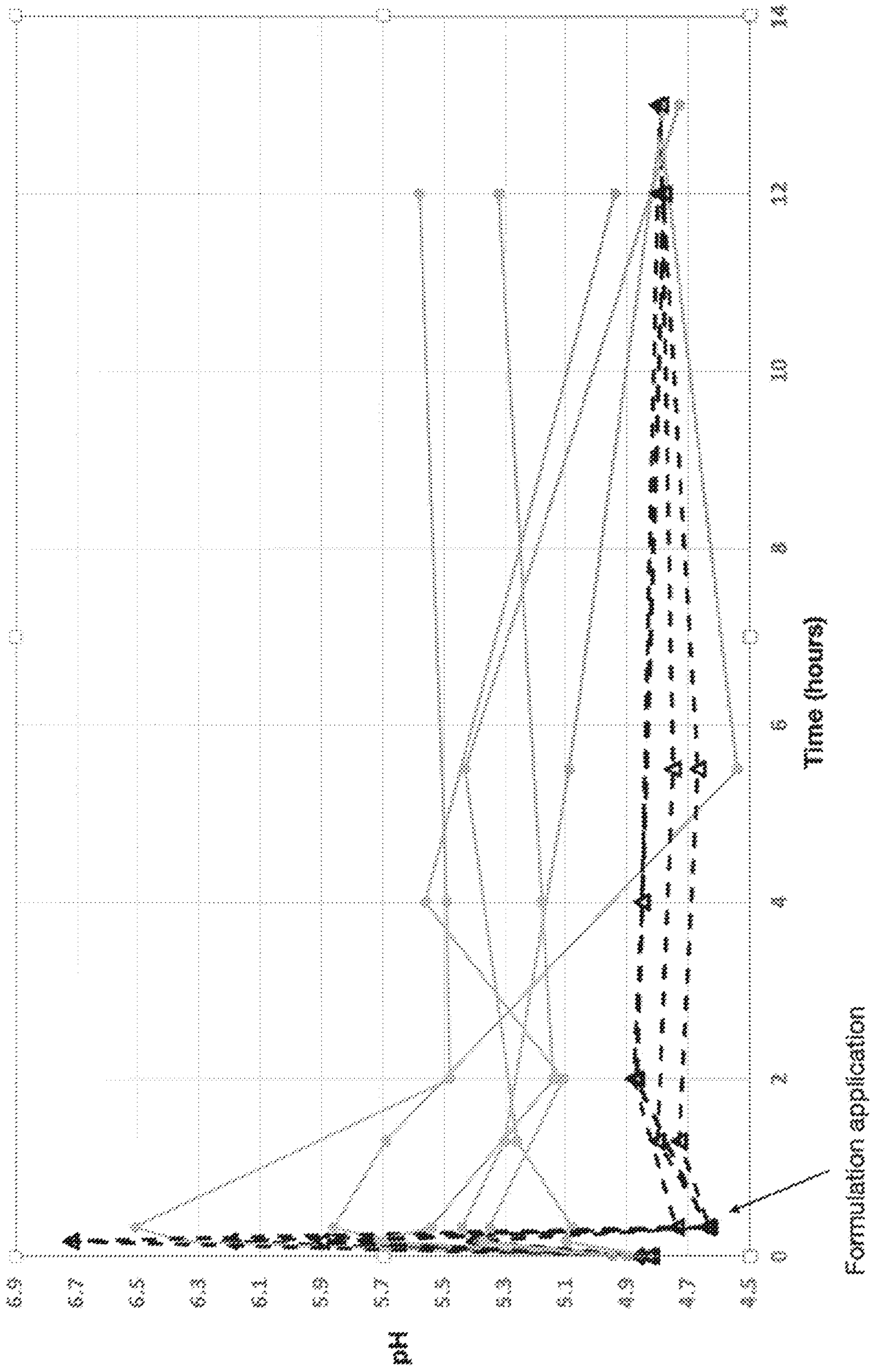
FIG. 3 is a graph showing the effect of an exemplary formulation provided herein on skin surface pH after initial pH disruption (due to skin washing with soap and water). Each solid line is a control without use of the formulation, and each dotted line shows the skin surface pH over 12 hours after application of the exemplary formulation.

Results are summarized in FIG. 3. The formulation applied was surprisingly observed to correct skin surface pH after initial pH disruption (due to skin washing with soap and water) and continue maintaining optimal skin surface pH for over 12 hours.

Example 4

Evaluation of Various Buffering Systems

This example evaluates various buffering systems for maintaining a stable pH on human skin over an extended period of time.

Several buffering systems were considered and evaluated:

- Lactic acid/lactate in the concentration range 5-30%.
- Glycolic acid/glycolate in the concentration range 5-30%.
- Lactic acid/lactate/citric acid/citrate in the concentration range 5-30%.
- Citric acid/citrate in the concentration range 2-30%.
- Citric acid/citrate/gluconic acid/gluconate in the concentration range 2-30%.

The buffering systems comprising small hydroxy acids such as glycolic and lactic acids were found to be more irritating for sensitive skin in initial tests. Glycolic and lactic acids also have lower than optimal pKa values, 3.83 and 3.86 respectively. Additionally, glycolic and lactic acids are readily absorbed by the skin, which could provide a challenge for maintaining stable pH over long time periods. Citric acid and gluconic acid are water soluble and have larger molecular weights, which limits their skin permeability. They were well tolerated on healthy and eczema affected skin. Gluconic acid pKa 3.86 was too low to provide strong buffer capacity at pH 4.7 on its own. Citric acid contains three carboxylic groups with pKa 3.13, 4.76, and 6.4, which are in the desirable pKa range for constructing a pH buffer capable of maintaining a pH range with optimal pH buffering capacity at around pH 4.7. Citric acid also remains charged within the optimal skin pH range, which further limits its skin permeability. In initial experiments, formulations constructed with buffers containing citric acid/sodium citrate and citric acid/gluconic acid/sodium citrate with adjusted ratios to result in pH 4.7 proved to be effective and well tolerated. The tolerability was, however, concentration dependent. By testing different concentrations, the optimal concentration and acid/base ratio was identified that provided strong buffer capacity at pH 4.7 and good tolerability. The buffers were further improved by the addition of supporting molecules that are capable of accepting hydrogen ions within the desirable pH range, such as fatty acids (for example, caprylic acid pKa 4.89, capric acid pKa 4.9, lauric acid pKa 5.3), carbohydrates (such as hyaluronic acid pKa between 3 and 4), ferulic acid pKa 4.61, and amino acids (pKa of the side chains of aspartic acid around 3.65 and glutamic acid 4.25).

What is claimed is:

1. A topical cream formulation with an optimal pH buffer capacity at around pH 4.7, the topical cream formulation exhibiting a pH buffering behavior, comprising:

a) a lipid phase comprising triglycerides, cetearyl alcohol, and ceteareth-20;

b) a dispersed aqueous phase comprising a buffer system including a plurality of acids and corresponding conjugate bases, wherein the buffer system comprises:

citric acid and sodium citrate in a combined amount of 2-10% by weight of the topical cream formulation, wherein the citric acid has pKa values of 3.13, 4.76, and 6.4; and gluconic acid in an amount of 0.1-1.0% by weight of the topical cream formulation, wherein the gluconic acid has a pKa of 3.86, wherein each acid of the plurality of acids has a molecular weight of at least 140 g/mol;

c) at least one supporting compound capable of accepting at least some hydrogen ions within a pH range between 3 and 5.5, wherein the at least one supporting compound comprises at least one medium chain fatty acid, at least one carbohydrate, at least one amino acid having a pKa between 3 and 5, or any combination thereof; and d) at least one skin barrier renewal component, at least one anti-inflammatory component, at least one anti-microbial component, at least one humectant, at least one emollient and/or emulsifier, or any combination thereof, wherein the cream formulation maintains a skin's surface pH of 4.2 to 5.0 for at least six hours following application to the skin's surface.

2. The topical cream formulation of claim 1, wherein the buffer system further comprises ferulic acid.

3. The topical cream formulation of claim 1, wherein the at least one supporting compound comprises at least one medium chain fatty acid having a pKa between 4.5 and 5.5.

4. The topical cream formulation of claim 1, wherein the at least one supporting compound comprises caprylic acid, capric acid, or lauric acid, or any combination thereof.

5. The topical cream formulation of claim 1, wherein the at least one supporting compound comprises at least one carbohydrate having a pKa between 3 and 4.

6. The topical cream formulation of claim 1, wherein the at least one supporting compound comprises hyaluronic acid.

7. The topical cream formulation of claim 1, wherein the at least one supporting compound comprises glutamic acid.

8. The topical cream formulation of claim 1, wherein at least one skin barrier renewal component comprises a ceramide complex, niacinamide, or phytosphingosine, or any combination thereof.

9. The topical cream formulation of claim 8, wherein the ceramide complex comprises ceramides, cholesterol, and at least one free fatty acid or a precursor thereof.

10. The topical cream formulation of claim 9, wherein the precursor of the at least one free fatty acid is sodium lauroyl lactylate.

11. The topical cream formulation of claim 1, wherein the at least one anti-inflammatory component or the at least one anti-microbial component comprises sunflower seed oil, coconut oil, shea butter, or colloidal oatmeal, or any combination thereof.

12. The topical cream formulation of claim 1, wherein the at least one humectant comprises hyaluronic acid, amino acids, glycerin, or xanthan gum, or any combination thereof.

13. The topical cream formulation of claim 1, wherein the at least one emollient and/or emulsifier comprises caprylic triglyceride, cetearyl alcohol, or ceteareth-20, or any combination thereof.

14. The topical cream formulation of claim 1, further comprising: sunflower seed oil; coconut oil; shea butter; and colloidal oatmeal.

15. The topical cream formulation of claim 1, wherein the optimal pH buffer capacity is at pH 4.7+/−0.3; and wherein the topical cream formulation, when applied to human skin, maintains a skin surface pH of 4.7+/−0.3.

16. The topical cream formulation of claim 1, wherein the plurality of acids is present in a total amount of between 1% and 30% by weight of the total cream formulation.

17. The topical cream formulation of claim 1, wherein the topical cream formulation is vegan.

18. A system, comprising: a container containing the topical cream formulation of claim 1.

19. The topical cream formulation of claim 1, wherein the buffer system further comprises at least one additional acid having a pKa between 3 and 6.5.

20. The topical cream formulation of claim 19, wherein the at least one additional acid comprises tartaric acid, mandelic acid, tropic acid, lactobionic acid, glucuronic acid, or ferulic acid, or any combination thereof.

21. A method comprising: applying the topical cream formulation of claim 1 to skin of a human, wherein the skin has a skin surface pH, and wherein the skin surface pH is maintained at around 4.7 for at least 6 hours.

* * * * *